United States Patent
Jacoby et al.

(10) Patent No.: US 7,250,536 B2
(45) Date of Patent: Jul. 31, 2007

(54) PROCESS FOR THE ISOMERISATION OF A CYCLOHEXENYL ALKYL OR ALKENYL KETONE

(75) Inventors: Denis Jacoby, Nyon (CH); Bessaa Neffah, Plan-les-Ouates (CH); Christian Chapuis, Mies (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 11/438,756

(22) Filed: May 22, 2006

(65) Prior Publication Data

US 2006/0211889 A1    Sep. 21, 2006

Related U.S. Application Data

(63) Continuation of application No. PCT/IB2004/003978, filed on Nov. 30, 2004.

(30) Foreign Application Priority Data

Dec. 16, 2003 (WO) ................ PCT/IB03/06118
Dec. 18, 2003 (EP) ................ 03029166

(51) Int. Cl.
*C07C 45/67* (2006.01)
*B01J 31/00* (2006.01)
*B01J 23/00* (2006.01)

(52) U.S. Cl. ............... 568/341; 502/150; 502/326

(58) Field of Classification Search ........... 568/341
See application file for complete search history.

(56) References Cited

U.S. PATENT DOCUMENTS

| | | | | |
|---|---|---|---|---|
| 4,226,892 A | | 10/1980 | Kovats et al. | 426/538 |
| 6,214,763 B1 * | | 4/2001 | Dobbs et al. | 502/155 |
| 6,313,365 B1 * | | 11/2001 | Hori et al. | 585/645 |
| 2002/0004615 A1 | | 1/2002 | Watanabe et al. | 568/34 |

FOREIGN PATENT DOCUMENTS

CH    537 352 A    7/1973
EP   1 162 190 A2  12/2001

OTHER PUBLICATIONS

Newbound et al. Open and Half-Open Ruthenocenes and Osmocenes. Organometallics, 1990, vol. 9, p. 2962-2972.*

* cited by examiner

*Primary Examiner*—Sikarl A. Witherspoon
(74) *Attorney, Agent, or Firm*—Winston & Strawn LLP

(57) ABSTRACT

The present invention relates to a process for the carbon-carbon double bond isomerisation of a 2-alkyl-cyclohex-3-enyl alkyl or alkenyl ketone into a mixture comprising the corresponding 2-alkyl-cyclohex-2-enyl ketones and the corresponding 2-alkylene-cyclohexyl ketones, using as catalyst a ruthenium complex obtainable by the reaction of an appropriate ruthenium organometallic precursor and an acid.

10 Claims, No Drawings

PROCESS FOR THE ISOMERISATION OF A CYCLOHEXENYL ALKYL OR ALKENYL KETONE

CROSS-REFERENCE TO RELATED APPLICATIONS

This application is a continuation of International application PCT/IB2004/003978 filed Nov. 30, 2004, the entire content of which is expressly incorporated herein by reference thereto.

TECHNICAL FIELD

The present invention relates to the field of organic synthesis. More particularly it provides a process for the isomerisation of a 2-alkyl-cyclohex-3-enyl alkyl or alkenyl ketone into a mixture comprising the corresponding 2-alkyl-cyclohex-2-enyl ketones and the corresponding 2-alkylene-cyclohexyl ketones, using as catalyst a complex obtainable by the reaction of an appropriate ruthenium organometallic precursor and an acid.

BACKGROUND

The compounds of formula (II) or (II'), as defined below, can be useful as perfuming ingredients or as starting material for the construction of compounds having a more complex skeleton.

The methods of preparation of said compounds reported in the prior art are in general quite long and expensive. Moreover, each of said methods allows to obtain only one or the other of said compounds. Consequently, to obtain said compounds a person skilled in the art has to carry out two separate processes with an evident loss of time.

It is therefore highly desirable to access such compounds by means of a simple and efficient isomerisation process wherein the starting material is an easily accessible material and it is possible to obtain both compounds (II) and (II').

To the best of our knowledge, in the prior art there is no report of an isomerisation process giving a direct access to compounds of formulae (II) and (II') at the same time.

SUMMARY OF THE INVENTION

The present invention now relates to a process for the summarization of a 2-alkyl-cyclohex-3-enyl alkyl or alkenyl ketone into a mixture comprising the corresponding 2-alkyl-cyclohex-2-enyl ketones and the corresponding 2-alkylene-cyclohexyl ketones, using as catalyst a complex obtainable by the reaction of an appropriate ruthenium organometallic precursor and an acid. The process can be also used to obtain optically active compounds. The invention also relates about the catalysts.

DETAILED DESCRIPTION OF THE PREFERRED EMBODIMENTS

In order to solve the problems aforementioned, the present invention provides a process for the isomerisation of a substrate of formula

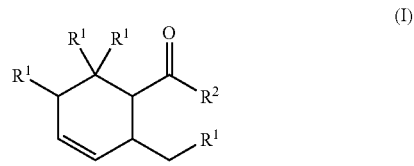

wherein each $R^1$ represents, simultaneously or independently, a hydrogen atom or a methyl group and $R^2$ represents a hydrogen atom linear or branched $C_{1-4}$ alkyl or a $C_{2-5}$ 1-alkenyl group;

into a mixture comprising at least one compound of formula (II) and at least one compound of formula (II')

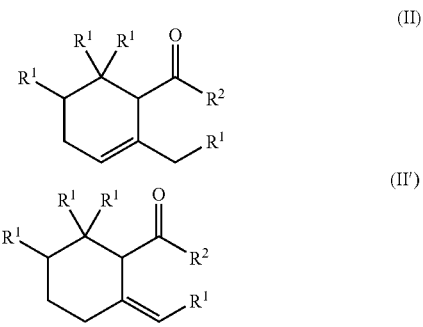

wherein $R^1$ and $R^2$ have the same meaning as indicated above;

said process being carried out in a non-coordinating or weakly coordinating medium, under an inert atmosphere and in the presence of a catalyst obtainable by the reaction of
a) a ruthenium precursor of the formula [Ru(diene)(allyl)$_2$], [Ru(dienyl)$_2$], [Ru(tetraene)(ene)] or [Ru(diene)(triene)]; and
b) a protic acid of formula HX, wherein X is a weakly- or non-coordinating anion; or a Lewis acid of formula B($R^3$)$_3$, wherein $R^3$ represents a fluoride or a phenyl group optionally substituted by one to five groups such as halide atoms or methyl or $CF_3$ groups, or a Lewis acid of formula $FeX_3$, $FeX_2$, $AgX$, $AlY_3$, $FeY_3$, $FeY_2$, $SnY_2$, $SnY_4$, $AgY$, $AgY_2$, $SbY_5$, $AsY_5$ or $PY_5$, X being a group as defined above and Y being a fluorine or chlorine atom;

in a non-coordinating or weakly coordinating medium and under an inert atmosphere, the molar ratio acid/ruthenium being comprised between 0.3 and 3.1.

Another compound which may be present in the mixture obtained by the invention's isomerisation process, and which is useful to be mentioned, is an enone of formula

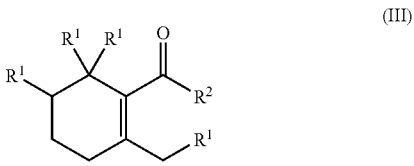

wherein $R^1$ and $R^2$ have the same meaning as indicated in formula (I). Said compound (III) is an optional constituent of the mixture obtained at the end of the isomerisation. In fact, the applicant has observed that the formation of said compound (III) depends on the specific experimental conditions, in particular on ratio Ru/acid, on the temperature and the duration of the reaction, or on the catalyst used and its concentration. In general, the compound (III) accounts for less than 2% of the weight of the final mixture. According to a preferred embodiment of the invention, the final mixture is devoid of said compound of formula (III).

According to a preferred embodiment of the invention the substrate is a compound of formula

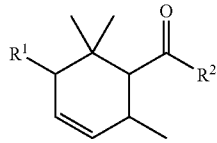
(IV)

wherein $R^1$ and $R^2$ have the same meaning as indicated in formula (I), preferably $R^1$ representing a hydrogen atom and $R^2$ representing a hydrogen atom or a methyl or $CH=CHCH_3$ group; and the mixture obtained comprises the corresponding compounds of formulae (V) and (V')

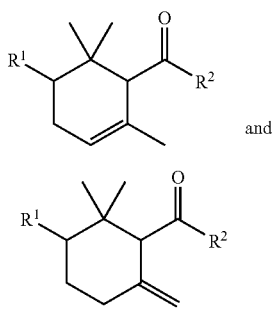
(V)

and (V')

wherein $R^1$ and $R^2$ have the same meaning as indicated for formula (IV).

In this embodiment, the optional ingredient, mentioned above, of the mixture would be of the formula

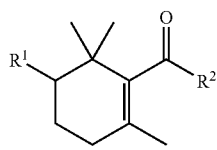
(VI)

wherein $R^1$ and $R^2$ have the same meaning as indicated for formula (VI).

Furthermore, it is also important to mention, regardless of the specific embodiments, than compounds of formula (I), as well as the corresponding compounds (II) or (II'), can be in an optically active form. In particular, compounds (I), (II) or (II') can be of formula

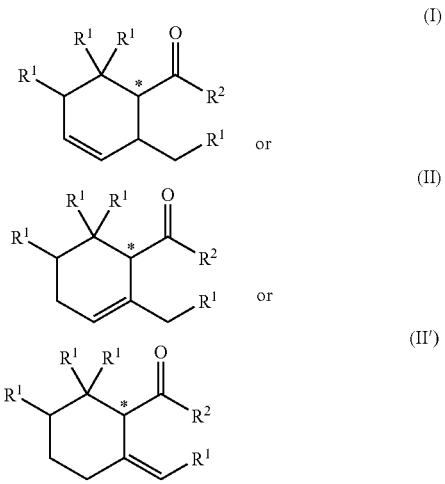

wherein $R^1$ and $R^2$ have the same meaning as indicated above and the asterisk means that said compounds are in an optically active form.

Specific examples of compound (I) optically active are (2E)-1-[(1S,2R)-2,6,6-trimethyl-3-cyclohexen-1-yl]-2-buten-1-one, (2E)-1-[(1S,2S)-2,6,6-trimethyl-3-cyclohexen-1-yl]-2-buten-1-one, 1-[(1S,2R)-2,6,6-trimethyl-3-cyclohexen-1-yl]-1-ethanone or 1-[(1S,2S)-2,6,6-trimethyl-3-cyclohexen-1-yl]-1-ethanone.

The catalyst is an essential element of the invention's process. As mentioned above said catalyst is obtainable by the reaction of an organometallic ruthenium precursor and a particular Lewis or protic acid in a non-coordinating or weakly coordinating medium and under an inert atmosphere.

As non-limiting examples of suitable ruthenium precursors one can cite compounds of general formula [Ru(diene)(allyl)$_2$] wherein "diene" stands for a $C_4$-$C_{20}$, preferably $C_4$-$C_{10}$, hydrocarbon group comprising two carbon-carbon double bonds, such as for example COD (cycloocta-1,5-diene) or NBD (norbornadiene), or yet hepta-1,4-diene, and "allyl" stands for a $C_3$-$C_{20}$, preferably $C_3$-$C_{10}$, hydrocarbon group comprising a fragment C=C—C$^-$, or C=C—C*, such as for example 2-allyl or 2-methallyl (see, for instance, J. P. Genet et al., cited references; M. O. Albers et al., Inorganic Synth., 1989, 26, 249; R. R. Schrock et al., J. Chem. Soc. Dalton Trans., 1974, 951).

Other appropriate ruthenium complexes include the compounds of the [Ru(dienyl)$_2$] type, wherein "dienyl" stands for a $C_4$-$C_{20}$, preferably $C_4$-$C_{15}$, hydrocarbon group comprising a carbon-carbon double bond and a fragment C=C—C$^-$, C=C—C* or C=C—O$^-$, such for example the pentadienyl, cyclopentadienyl, a substituted cyclopentadienyl (such as pentamethyl-cyclopentadienyl), 2,4-dimethyl-pentadienyl, 2,3,4-trimethylpentadienyl, 2,4-di(tert-butyl)-pentadienyl or yet 2,4-dimethyl-1-oxapentadienyl (see, for example, R. D. Ernst et al., J. Organometallic Chem., 1991, 402, 17; L. Stahl et al., Organometallic 1983, 2, 1229; T. Schmidt et al., J. Chem. Soc. Chem. Commun., 1991, 1427; T. D. Newbound et al., Organometallics, 1990, 9, 2962), or yet 2,5-cyclooctadienyl or 2,5-cycloheptadienyl (see, for example, P. Pertici et al., J. Chem. Soc. Dalton Trans., 1980, 1961).

Yet other appropriate ruthenium complexes are of formula [Ru(diene)(triene)], wherein "triene" stands for a $C_7$-$C_{20}$, preferably $C_7$-$C_{12}$, hydrocarbon group comprising three carbon-carbon double bonds, such as for example cycloocta-1,3,5-triene (COT), benzene or a substituted benzene such as a hexa-methyl-benzene. The preferred trine is COT.

Another appropriate ruthenium complex is of formula [Ru(tetraene)(ene)], wherein "tetraene" stands for a $C_8$-$C_{20}$, preferably $C_8$-$C_{12}$, hydrocarbon group comprising four carbon-carbon double bonds, such as for example cycloocta-1,3,5,7-tetraene, and "ene" stands for a $C_2$-$C_{10}$, preferably $C_4$-$C_8$, hydrocarbon group comprising one carbon-carbon double bond, such as for example cyclooctene or cyclohexene.

Following a preferred embodiment of the invention, there is used as the Ru precursor, the compound of formula [Ru(COD)(2-methallyl)$_2$], [Ru(COD)(COT)], [Ru(2,4-dimethylpentadienyl)$_2$] (e.g. L. Stahl et al. or T. D. Newbound et al., references cited) or the [Ru(2,4-dimethyl-1-oxapentadienyl)$_2$] complexes (e.g. T. Schmidt et al., reference cited). [Ru(COD)(2-methallyl)$_2$], the preparation of which was first reported by J. Powell et al., in J. Chem. Soc., (A), 1968, 159, proved quite convenient from a practical point of view.

In the process for the preparation of the catalyst there is used an acid, said acid is believed to cationize the ruthenium precursor.

A first type of suitable acids employed in the preparation of the catalyst is of the protic type. Said protic acid must have a weakly- or non-coordinating anion. By the expression "weakly- or non-coordinating anion" we mean here an anion which does not interact significantly, under the reaction conditions, with the catalyst, such a notion is well understood by a person skilled in the art of the catalysis. In other words, a weakly- or non-coordinating anion is an anion which does not coordinate at all the Ru center of the catalyst or which has a coordination stability constant inferior to that of the substrate of formula (I).

Non-limiting examples of protic acids suitable for the preparation of the catalyst are acid of formula HX, wherein X is a $ClO_4^-$, $R^4SO_3^-$, wherein $R^4$ is a chlorine of fluoride atom or a $C_1$-$C_8$ fluoroalkyl or fluoroaryl group, $BF_4^-$, $PF_6^-$, $SbCl_6^-$, $AsCl_6^-$, $SbF_6^-$, $AsF_6^-$ or $BR_4^-$, wherein R is a phenyl group optionally substituted by one to five groups such as halide atoms or methyl or $CF_3$ groups.

According to a preferred embodiment of the invention, the weakly- or non-coordinating anion is $BF_4^-$, $PF_6^-$, $C_6F_5SO_3^-$, $CF_3SO_3^-$ or yet $B[3,5-(CF_3)_2C_6H_4]_4^-$, even more preferably $BF_4^-$.

Such protic acids can be used in the form of the corresponding etherates (for example $HBF_4R^5{}_2O$, $R^5$ being a $C_1$-$C_5$ hydrocarbon group such as $C_2H_5$ or $C_4H_9$). These etherates are commercial products, or they can be prepared by reacting AgX with HCl in a solvent containing a dialkylether, for example a mixture of dichloromethane and diethylether. As the silver chloride precipitates, it provides the etherate solution of the acid, which can then be used according to the invention in the reaction with the ruthenium precursor.

A second type of suitable acid employed in the preparation of the catalyst is of the Lewis type. Suitable examples of such acids are $FeCl_3$, $AlCl_3$, $SbF_5$, $AsF_5$ or $PF_5$, AgF, $Fe(CF_3SO_3)_3$, $AgBF_4$, $SnCl_2$, $BF_3$ or $BMe_3$.

These acids can be in an anhydrous form or, for some of them, also in a hydrate form. Furthermore, the boron or aluminum derivative, especially $BF_3$, could be in the form of anyone of its adduct with an ether or carboxylic acid, such as $R^6{}_2O$ or $R^7COOH$, wherein $R^6$ is a $C_1$-$C_5$ alkyl group and $R^7$ is a $C_1$-$C_{20}$ alkyl group. According to a particular embodiment of the invention, preferred Lewis acid is $BF_3$ or a $BF_3$ adduct with $Et_2O$, $Bu_2O$ or AcOH.

According to the above, in the preparation of the catalyst, the acid and the Ru precursor are reacted in a molar ratio comprised between 0.3 and 3.1. According to a preferred embodiment of the invention said ratio is comprised between approximately 0.5 and 2.

In order not to compromise its effectiveness, the catalyst should also be prepared in a non-coordinating or weakly coordinating solvent and under an inert atmosphere. By the expression "non-coordinating or weakly coordinating solvent" we mean here a solvent which does not deactivate significantly the catalyst and allows the substrate to interact with the catalyst, such a notion is well understood by a person skilled in the art of the catalysis. In other words, a weakly- or non-coordinating solvent is a solvent which does not coordinate at all the Ru center of the catalyst or which has a coordination stability constant inferior to that of the substrate of formula (I).

In general, any solvent which is inert under the experimental conditions and is able to solubilize the substrate and catalyst is particularly appreciated. In a particular embodiment of the invention, such a solvent is a chlorinated hydrocarbon, saturated or unsaturated hydrocarbon, an ether, an ester, a carboxylic acid, a weakly coordinating ketone (sterically hindered ketone) or a substrate of formula (I) or a mixture thereof. Specific examples of such solvents are $CH_2Cl_2$, heptane, octane, dibutylether, butylacetate, acetic acid, teramyl methylether, diisopropylketone or yet a compound of formula (IV) as defined above.

By the expression "inert atmosphere" we mean here an atmosphere which is not reactive towards the catalyst, and in particular an atmosphere whose oxygen content is lower than 200 ppm, and preferably not above 100 ppm.

To the best of our knowledge, the catalysts obtained according to a process described above and wherein the acid is a Lewis acid, as defined above, are new compounds. Said catalysts are also an object of the present invention. Preferred Lewis acid are $BF_3$, $BF_3.Et_2O$, $BF_3.Bu_2O$ or $BF_3.(AcOH)_2$. Preferred ruthenium precursor are the complexes [Ru(COD)(2-methallyl)$_2$], [Ru(COD)(COT)], [Ru(2,4-dimethylpentadienyl)$_2$] or [Ru(2,4-dimethyl-1-oxapentadienyl)$_2$], and in particular [Ru(COD)(2-methallyl)$_2$].

The invention's process should also be carried out in a non-coordinating or weakly coordinating solvent and under an inert atmosphere. Said solvent and atmosphere are defined as above for the formation of the catalyst.

The amount in which the catalyst may be employed in the invention's process is typically comprised between 0.01 and 2 molar %, relative to the substrate. In a preferred embodiment of the process of the invention the catalyst is used in a concentration comprised between about 0.05 and 1 molar %. More preferably, the amount of the catalyst can be comprised between approximately 0.1 and 0.4 molar %. The use of high amounts of catalyst may lend to the presence of the compound of formula (III) in the obtained mixture.

The temperature at which the process of the invention can be carried out is comprised between 60° C. and the refluxing temperature of the solvent or of the substrate. Preferably, the temperature is in the range of between 60° C. and 180° C., more preferably between 110° C. and 165° C., and even more preferably between 110° and 150° C. Of course, a person skilled in the art is also able to select the preferred temperature as a function of the melting and boiling point of the starting and final products as well as of the solvent.

However it has to be said that when the process temperature is in the range comprised between 150° and 180° C. the mixture obtained at the end of the process may contain an appreciable amount of compound of formula (III), especially if the reaction is left at such temperature even after the conversion of the substrate is no longer observed.

EXAMPLES

The invention will now be described in further detail by way of the following examples, wherein the abbreviations have the usual meaning in the art, the temperatures are indicated in degrees centigrade (° C.).

Example 1

Summarization of 1-(2,6,6-trimethyl-3-cyclohexen-1-yl)-1-ethanone in the presence of a catalyst obtained using a protic acid To trans 1-(2,6,6-trimethyl-3-cyclohexen-1-yl)-1-ethanone (4.52 mol; trans/cis=94/5 to 99/1, purity≧99%) stirred under nitrogen at 20° C. was added $HBF_4.OEt_2$ (4.54 mmol of $HBF_4$) and $[Ru(COD)(methallyl)_2]$ (4.54 mmol) was added consecutively. The resulting solution was heated to 130° C. and stirred over 30 minutes at 130° C. under nitrogen. Afterwards, the resulting mixture was cooled to 20° C. and there was obtained a mixture comprising (% by weight of the final mixture, obtained by GC analysis):

| | |
|---|---|
| trans 1-(2,6,6-trimethyl-3-cyclohexen-1-yl)-1-ethanone | 6% |
| cis 1-(2,6,6-trimethyl-3-cyclohexen-1-yl)-1-ethanone | 1% |
| 1-(2,6,6-trimethyl-2-cyclohexen-1-yl)-1-ethanone | 86% |
| 1-(2,2-dimethyl-6-methyene-1-cyclohexyl)-1-ethanone | 2% |
| 1-(2,6,6-trimethyl-1-cyclohexen-1-yl)-1-ethanone | 2% |

Example 2

Isomerisation of 1-(2,6,6-trimethyl-3-cyclohexen-1-yl)-1-ethanone in the presence of a catalyst obtained using a Lewis acid To trans 1-(2,6,6-trimethyl-3-cyclohexen-1-yl)-1-ethanone (4.52 mol; trans/cis=94/5 to 99/1, purity≧99%) stirred under nitrogen at 20° C. was added $BF_3.(AcOH)_2$ (2.27 mmol of $BF_3$) and $[Ru(COD)(methallyl)_2]$ (2.27 mmol) was added consecutively. The resulting solution was heated to 130° C. and stirred over 30 minutes at 130° C. under nitrogen. Afterwards, the resulting mixture was cooled to 20° C. and there was obtained a mixture comprising (% by weight of the final mixture, obtained by GC analysis):

| | |
|---|---|
| trans 1-(2,6,6-trimethyl-3-cyclohexen-1-yl)-1-ethanone | 7% |
| cis 1-(2,6,6-trimethyl-3-cyclohexen-1-yl)-1-ethanone | 1% |
| 1-(2,6,6-trimethyl-2-cyclohexen-1-yl)-1-ethanone | 87% |
| 1-(2,2-dimethyl-6-methyene-1-cyclohexyl)-1-ethanone | 2% |
| 1-(2,6,6-trimethyl-1-cyclohexen-1-yl)-1-ethanone | not observed |

Example 3

Summarization of 1-(2,6,6-trimethyl-3-cyclohexen-1-yl)-2-buten-1-one in the presence of a catalyst obtained using a Lewis acid To trans 1-(2,6,6-trimethyl-3-cyclohexen-1-yl)-2-buten-1-one (25 g; 130 mmol; trans:cis 98:2; purity≧99%) stirred under nitrogen at 20° C. was added $BF_3.(AcOH)_2$ (0.65 mmol) and $[Ru(COD)(methallyl)_2]$ (0.65 mmol) are added consecutively. The resulting solution was heated to 130° C. and stirred over 60 minutes at 130° C. under nitrogen. Then the resulting mixture is cooled to 20° C. and there was obtained a mixture comprising (% by weight of the final mixture, obtained by GC analysis):

| | |
|---|---|
| trans 1-(2,6,6-trimethyl-3-cyclohexen-1-yl)-2-buten-1-one | 9% |
| 1-(2,6,6-trimethyl-2-cyclohexen-1-yl)-2-buten-1-one | 86% |
| 1-(2,2-dimethyl-6-methyene-1-cyclohexyl)-2-buten-1-one | 1% |
| 1-(2,6,6-trimethyl-1-cyclohexen-1-yl)-2-buten-1-one | not observed |

What is claimed is:
1. A process for the isomerisation of a substrate of formula

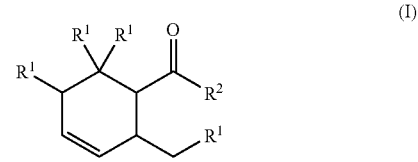

wherein each $R^1$ represents, simultaneously or independently, a hydrogen atom or a methyl group and $R^2$ represents a hydrogen atom linear or branched $C_{1-4}$ alkyl or a $C_{2-5}$ 1-alkenyl group;
into a mixture comprising at least one compound of formula (II) and at least one compound of formula (II')

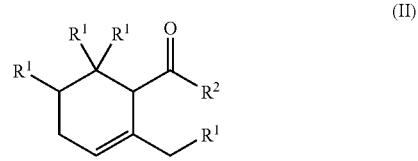

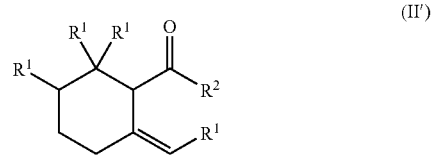

wherein $R^1$ $R^2$ have the same meaning as indicated above;
said process being carried out in a non-coordinating or weakly coordinating medium, under an inert atmosphere and in the presence of a catalyst obtained by the reaction of
a) a ruthenium precursor of the formula $[Ru(diene)(allyl)_2]$, $[Ru(dienyl)_2]$, $[Ru(tetraene)(ene)]$ or $[Ru(diene)(triene)]$; and b) a protic acid of formula HX, wherein X is a weakly-or non-coordinating anion; or a Lewis acid of formula $B(R^3)_3$, wherein $R^3$ represents a fluoride or a phenyl group optionally substituted by one to five groups such as halide atoms or methyl or $CF_3$ groups, or a Lewis acid of formula $FeX_3$, $FeX_2$, $AgX$, $AlY_3$, $FeY_3$, $FeY_2$, $SnY_2$, $SnY_4$, $AgY$, $AgY_2$, $SbY_5$, $AsY_5$ or $PY_5$, X being a group as defined above arid Y being a fluorine or chlorine atom;

in a non-coordinating or weakly coordinating medium and under an inert atmosphere, the molar ratio acid/ruthenium being comprised between 0.3 and 3.1.

2. A process according to claim 1, wherein compounds (I), (II) or (II') are of formula

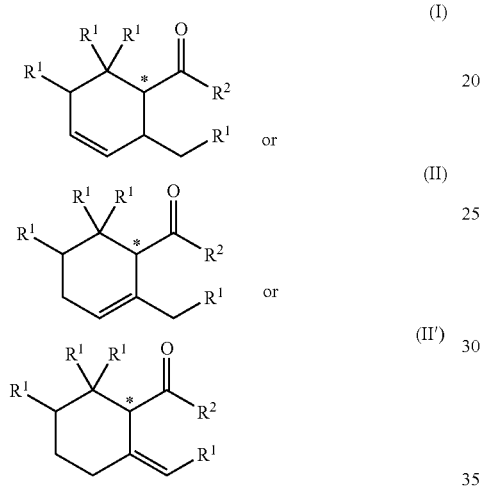

wherein $R^1$ and $R^2$ have the same meaning as in claim 1 and the asterisk means that said compounds are in an optically active form.

3. A process according to claim 1, wherein the substrate is of formula

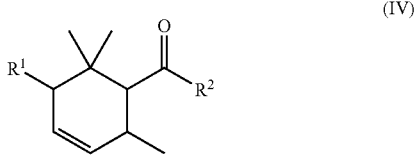

wherein $R^1$ and $R^2$ have the same meaning as indicated in claim 1; and the mixture obtained comprises the corresponding compounds of formulae (V) and (V')

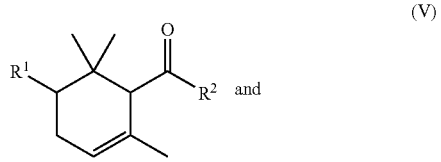

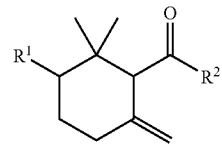

wherein $R^1$ and $R^2$ have the same meaning as indicated in claim 1.

4. A process according to claim 3, wherein $R^1$ represents a hydrogen atom and $R^2$ represents a hydrogen atom or a methyl or $CH=CHCH_3$ group.

5. A process according to claim 1, wherein the ruthenium precursor is a compounds of general formula
   i) $[Ru(diene)(allyl)_2]$ wherein "diene" stands for COD (cycloocta-1,5-diene), NBD (norbornadiene) or hepta-1,4-diene, and "allyl" stands for 2-allyl or 2-methallyl;
   ii) $[Ru(dienyl)_2]$ wherein "dienyl" stands for pentadienyl, 2,4-dimethylpentadienyl, 2,3,4-trimethylpentadienyl, 2,4-di(tert-butyl)-pentadienyl, 2,4-dimethyl-1-oxapentadienyl or 2,5-cyclooctadienyl or 2,5-cycloheptadienyl;
   iii) $[Ru(diene)(triene)]$ wherein "diene" has the same meaning as above and "triene" stands for cycloocta-1, 3,5-triene (COT); or
   iv) $[Ru(tetraene)(ene)]$, wherein "tetraene" stands for cycloocta-1,3,5,7-tetraene and "ene" stand for cyclooctene or cyclohexene.

6. A process according to claim 1, wherein X is a $ClO_4^-$, $R^4SO_3^-$, wherein $R^4$ is a chlorine of fluoride atom or an $C_1$-$C_8$ fluoroalkyl or fluoroaryl group, $BF_4^-$, $PF_6^-$, $SbCl_6^-$, $AsCl_6^-$, $SbF_6^-$, $AsF_6^-$ or $BR_4^-$, wherein R is a phenyl group optionally substituted by one to five groups such as halide atoms or methyl or $CF_3$ groups.

7. A process according to claim 1, wherein the acid HX is $HBF_4Et_2O$.

8. A process according to claim 1, wherein the Lewis acid is $FeCl_3$, $AlCl_3$, $SbF_5$, $AsF_5$ or $PF_5$, $AgF$, $Fe(CF_3SO_3)_3$, $AgBF_4$, $SnCl_2$, $BF_3$, BMe3 or an add of $BF_3$ with an ether or carboxylic acid $R^6_2O$ or $R^7COOH$, wherein $R^6$ is a $C_1$-$C_5$ alkyl group and $R^7$ is a $C_1$-$C_{20}$ alkyl group.

9. A catalyst obtained by the reaction of
   a) a ruthenium precursor of the formula $[Ru(diene)(allyl)_2]$, $[Ru(dienyl)_2]$, $[Ru(tetraene)(ene)]$ or $[Ru(diene)(triene)]$; and
   b) a Lewis acid of formula $B(R^3)_3$, wherein $R^3$ represents a fluoride or a phenyl group optionally substituted by one to five groups such as halide atoms or methyl or $CF_3$ groups, or a Lewis acid of formula $FeX_3$, $FeX_2$, $AgX$, $AlY_3$, $FeY_3$, $FeY_2$, $SnY_2$, $SnY_4$, $AgY$, $AgY_2$, $SbY_5$, $AsY_5$ or $PY_5$, X being a group as defined above and Y being a fluorine or chlorine atom;

the molar ratio acid/ruthenium being comprised between 0.3 and 3.1 and the reaction being carried out in a non-coordinating or weakly coordinating medium and under an inert atmosphere.

10. A catalyst according to claim 9, wherein the Lewis acid is $BE_3$, $BF_3.Et_2O$, $BF_3.Bu_2O$ or $BF_3.(AcOH)_2$.

* * * * *

UNITED STATES PATENT AND TRADEMARK OFFICE
CERTIFICATE OF CORRECTION

PATENT NO. : 7,250,536 B2  Page 1 of 1
APPLICATION NO. : 11/438756
DATED : July 31, 2007
INVENTOR(S) : Jacoby et al.

It is certified that error appears in the above-identified patent and that said Letters Patent is hereby corrected as shown below:

Column 8:
Line 59, change "$R^1\ R^2$" to -- $R^1$ and $R^2$ --.

Column 9:
Line 8, after "a group as defined above", change "arid" to -- and --.

Column 10:
Line 32, after "6. A process according to claim 1, wherein X is a", change "$ClO_4^-$," to -- $ClO_4^-$, --.
Line 42, after "$AgBF_4$, $SnCl_2$, $BF_3$, BMe3 or an", change "add" to -- adduct --.
Line 62, after "acid is $BE_3$," change "$BF_3.Et_2O$, $BF_3.Bu_2O$ or $BF_3.(AcOH)_2$." to -- $BF_3\ Et_2O$, $BF_3\ Bu_2O$ or $BF_3\ (AcOH)_2$. --.

Signed and Sealed this

Eighteenth Day of September, 2007

JON W. DUDAS
*Director of the United States Patent and Trademark Office*